(12) United States Patent
Inukai et al.

(10) Patent No.: US 11,110,249 B2
(45) Date of Patent: Sep. 7, 2021

(54) ASSISTANCE SYSTEM, ASSISTANCE METHOD, ASSISTANCE PROGRAM, AND RECORDING MEDIUM HAVING ASSISTANCE PROGRAM RECORDED THEREON

(71) Applicant: TERUMO KABUSHIKI KAISHA, Tokyo (JP)

(72) Inventors: Takito Inukai, Shizuoka (JP); Yasushi Kinoshita, Shizuoka (JP); Yoshinobu Isaka, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/759,435

(22) PCT Filed: Jul. 31, 2018

(86) PCT No.: PCT/JP2018/028722
§ 371 (c)(1),
(2) Date: Apr. 27, 2020

(87) PCT Pub. No.: WO2019/150609
PCT Pub. Date: Aug. 8, 2019

(65) Prior Publication Data
US 2021/0046280 A1 Feb. 18, 2021

(30) Foreign Application Priority Data
Feb. 1, 2018 (JP) .............................. JP2018-016151

(51) Int. Cl.
*A61M 25/00* (2006.01)
*A61B 34/10* (2016.01)

(52) U.S. Cl.
CPC ... *A61M 25/0041* (2013.01); *A61B 2034/108* (2016.02); *A61M 2210/125* (2013.01); *A61M 2210/127* (2013.01)

(58) Field of Classification Search
CPC .. A61M 25/01; A61M 25/0041; A61M 25/00; A61M 25/0009; A61M 25/0105;
(Continued)

(56) References Cited

U.S. PATENT DOCUMENTS 5,476,453 A  12/1995 Mehta
9,480,813 B2  11/2016 Fukuoka et al.
(Continued)

FOREIGN PATENT DOCUMENTS

CN  103566452 A  2/2014
JP  H05154202 A  6/1993
(Continued)

OTHER PUBLICATIONS

International Search Report (PCT/ISA/210) dated Oct. 30, 2018, by the Japanese Patent Office as the International Searching Authority for International Application No. PCT/JP2018/028722, and an English language translation of the International Search Report.
(Continued)

*Primary Examiner* — Nilay J Shah
(74) *Attorney, Agent, or Firm* — Buchanan Ingersoll & Rooney PC

(57) ABSTRACT

An assistance system includes a schedule information acquisition unit that acquires disease information on the surgery and blood vessel information relating to a shape of a portion capable of applying a backup force to the catheter by coming into contact with the catheter in a blood vessel of the patient, a past information acquisition unit that acquires a shape of a catheter used for a past similar surgery having the disease information coinciding with that of the surgery and having
(Continued)

the blood vessel information similar to that of the surgery, and a proposal unit that corrects the shape of the catheter used for the past similar surgery, based on a comparison result obtained by comparing the blood vessel information on the surgery with the blood vessel information on the past similar surgery, and that proposes a catheter having the corrected shape, as the catheter to be used for the surgery.

6 Claims, 9 Drawing Sheets

(58) Field of Classification Search
CPC ...... A61M 2210/125; A61M 2210/127; A61M 25/001; A61B 5/0044; A61B 1/00002; A61B 1/00004; A61B 34/10; A61B 34/20; A61B 2034/108; A61B 1/045; A61B 5/103; A61B 2034/107; G06G 7/60
See application file for complete search history.

(56) References Cited

U.S. PATENT DOCUMENTS

| | | |
|---|---|---|
| 2006/0161177 A1 | 7/2006 | Worley et al. |
| 2011/0077530 A1 | 3/2011 | Takagi et al. |
| 2011/0257630 A1 | 10/2011 | Johnson |
| 2012/0203056 A1* | 8/2012 | Corbett ................. A61M 1/122 600/16 |
| 2014/0025041 A1 | 1/2014 | Fukuoka et al. |
| 2017/0035514 A1 | 2/2017 | Fox et al. |
| 2018/0085167 A1* | 3/2018 | Goyal .................... A61B 34/00 |

FOREIGN PATENT DOCUMENTS

| | | |
|---|---|---|
| JP | 4026158 B1 | 12/2007 |
| JP | 2011087912 A | 5/2011 |
| JP | 3173720 U | 2/2012 |
| WO | 2017/139894 A1 | 8/2017 |

OTHER PUBLICATIONS

Written Opinion (PCT/ISA/237) dated Oct. 30, 2018, by the Japanese Patent Office as the International Searching Authority for International Application No. PCT/JP2018/028722, and an English language translation of the Written Opinion.

An English Translation of the Written Opinion of the International Searching Authority (Form PCT/ISA/237) dated Oct. 30, 2018, by the Japanese Patent Office in corresponding International Application No. PCT/JP2018/028725. (5 pages).

The First Office Action issued by the National Intellectual Property Adminstration in corresponding Chinese Patent Application No. 2018800767965 dated Jan. 20, 2021 (12 pages including partial English translation).

* cited by examiner

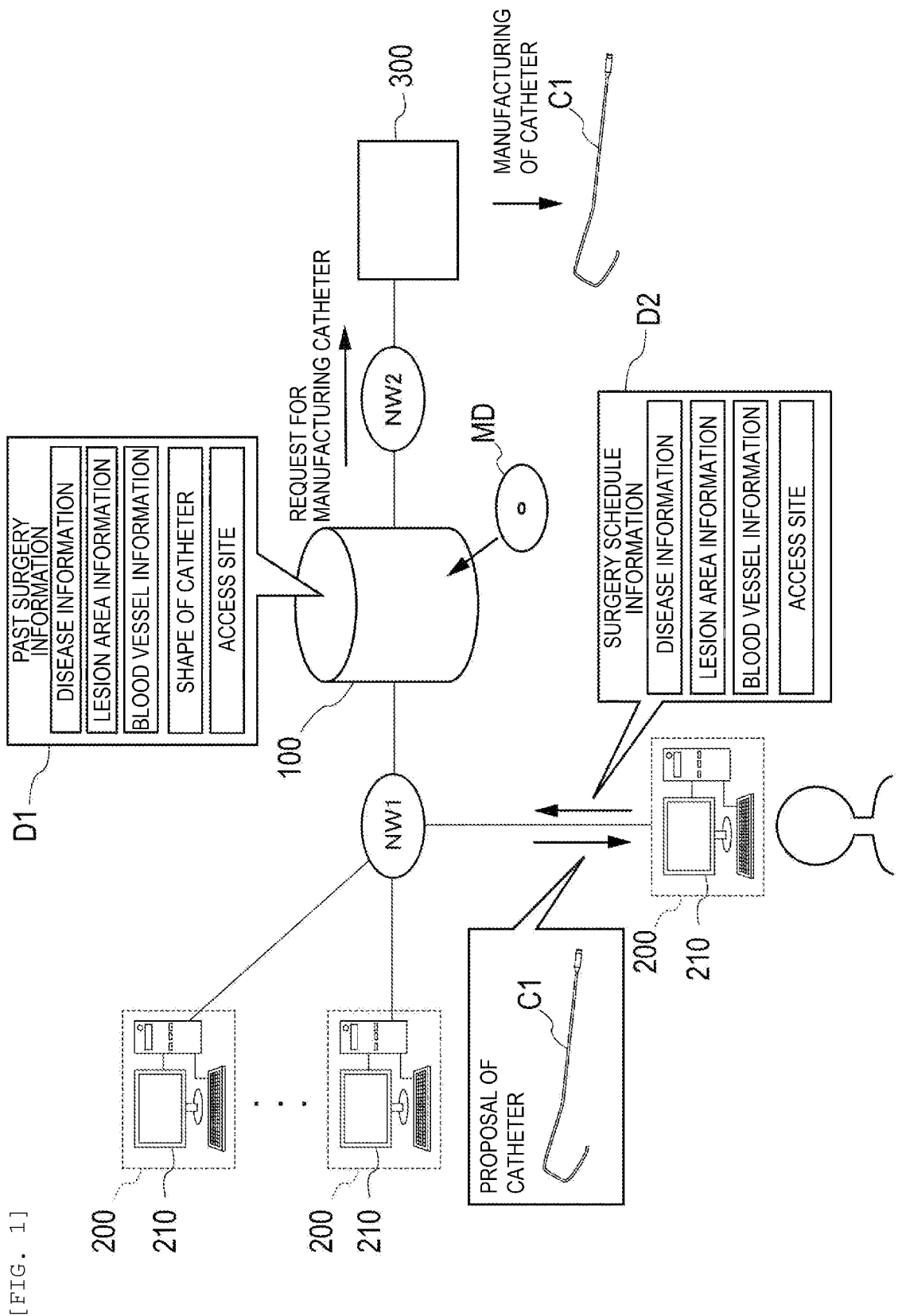
[FIG. 1]

[FIG. 2A]

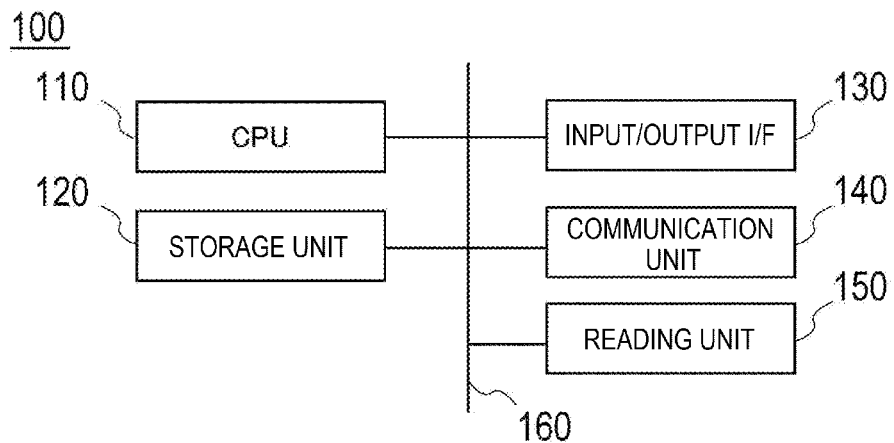

[FIG. 2B]

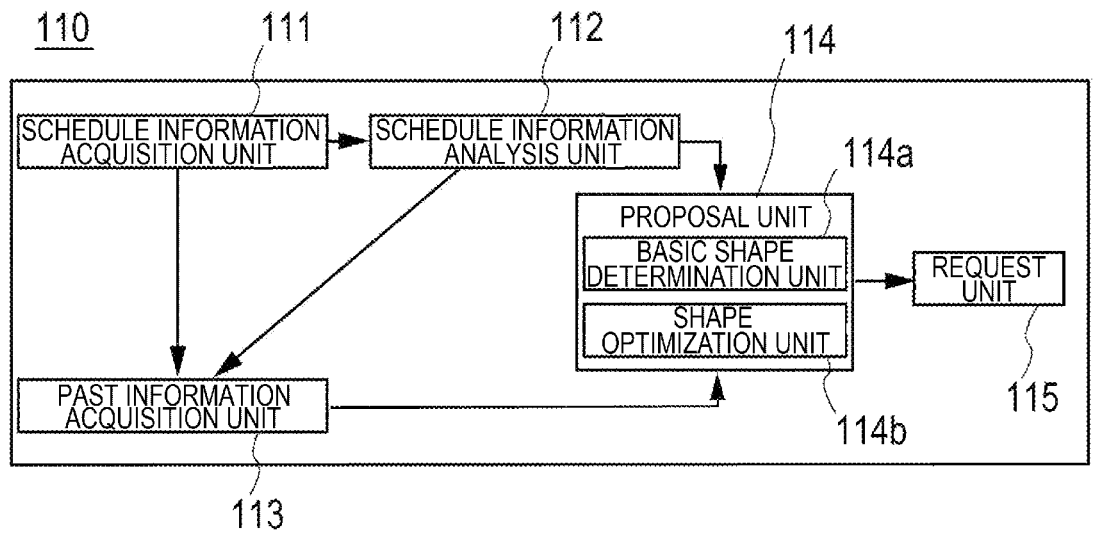

| No | DISEASE INFORMATION | | LESION AREA INFORMATION | BLOOD VESSEL INFORMATION | SHAPE OF CATHETER | | | ACCESS SITE |
|---|---|---|---|---|---|---|---|---|
| | DISEASE NAME | DISEASE SITE | | | BASIC SHAPE | DISTAL PORTION DIMENSION | OUTER DIAMETER | |
| 1 | ISCHEMIC MYOCARDIAL INFARCTION | LCX AORTIC ROOT | LESION AREA IMAGE | BLOOD VESSEL IMAGE | JL | × × × | 6 Fr | RIGHT Radial |
| 2 | ISCHEMIC MYOCARDIAL INFARCTION | LMD | LESION AREA IMAGE | BLOOD VESSEL IMAGE | JL | × × × | 7 Fr | RIGHT Femoral |
| 3 | CARDIAC INSUFFICIENCY | RCA | LESION AREA IMAGE | BLOOD VESSEL IMAGE | AL | × × × | 6 Fr | LEFT Radial |
| 4 | ARRHYTHMIA | LMT | LESION AREA | BLOOD VESSEL | IL | × × × | 7 Fr | LEFT Radial |

[FIG. 4A]
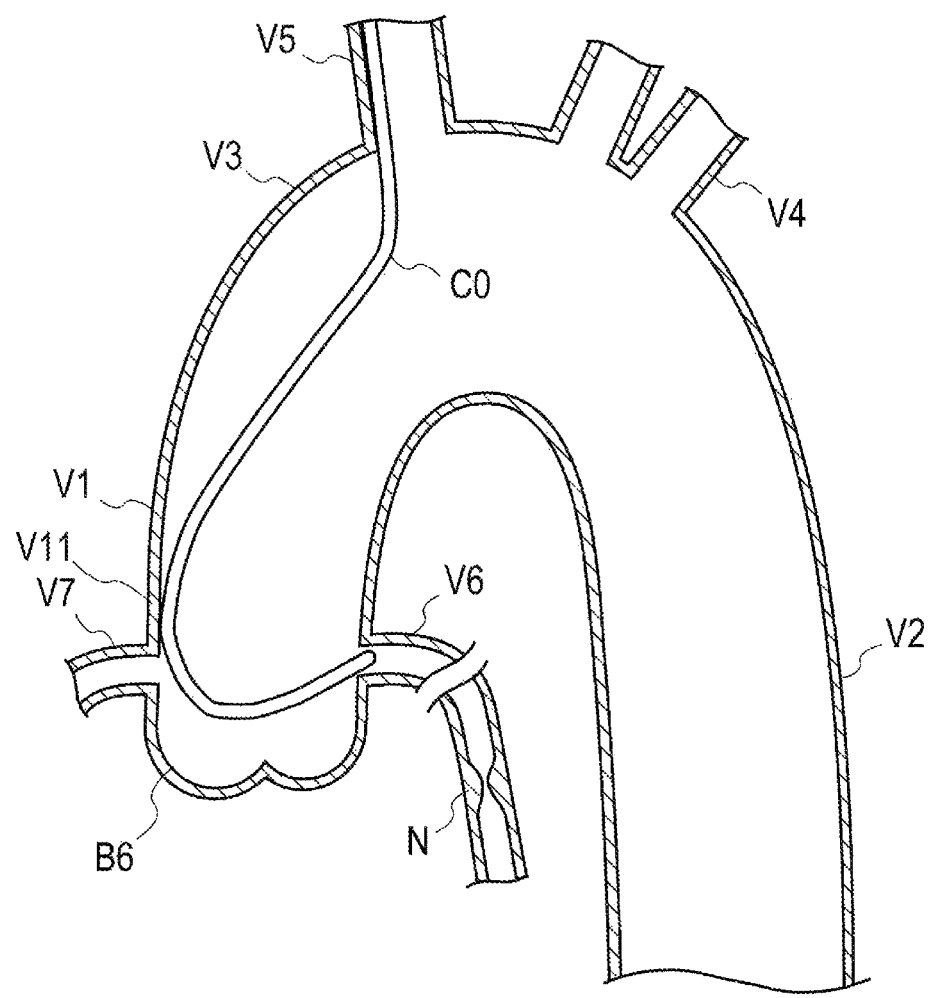

[FIG. 4B]
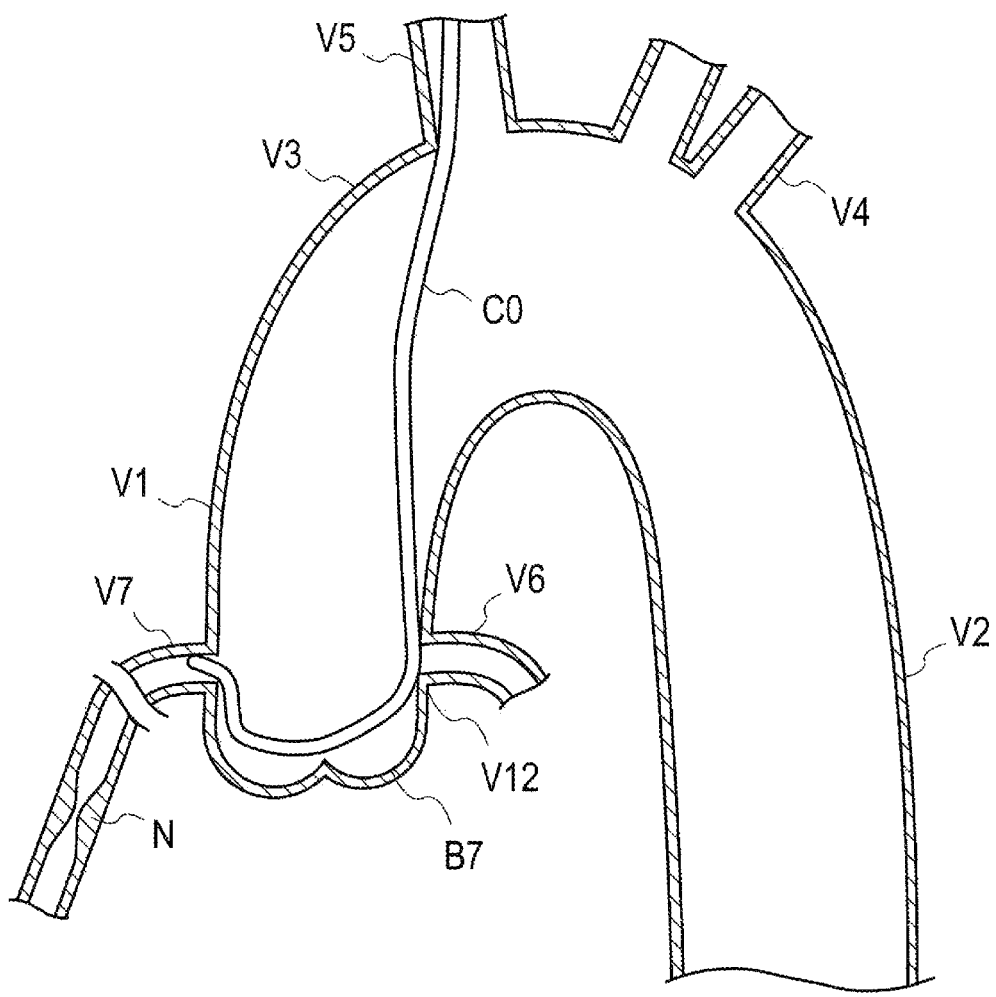

[FIG. 5A]
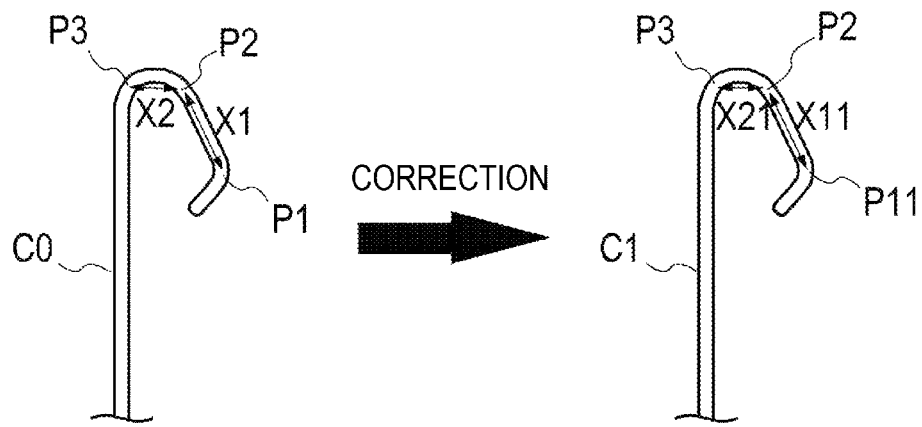
[FIG. 5B]
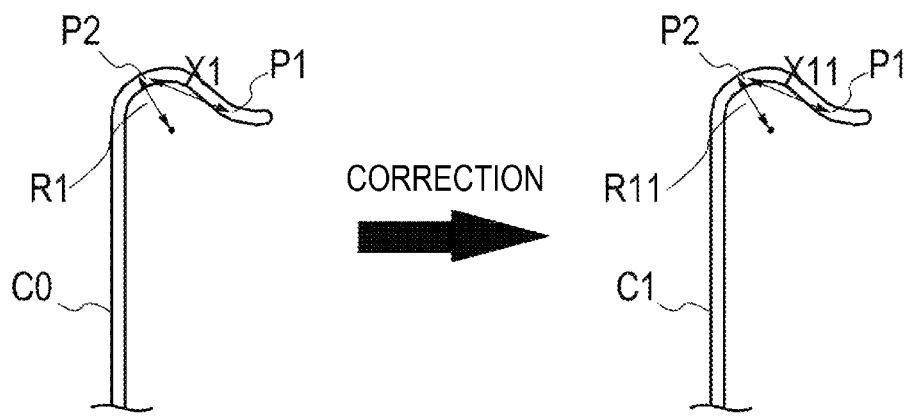
[FIG. 5C]
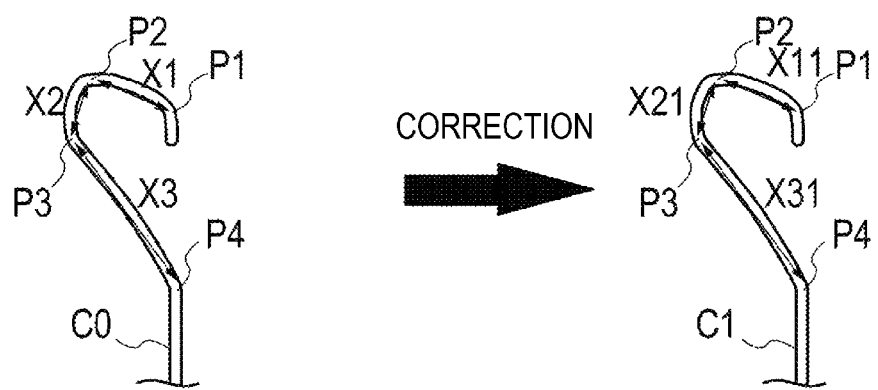

[FIG. 6A]
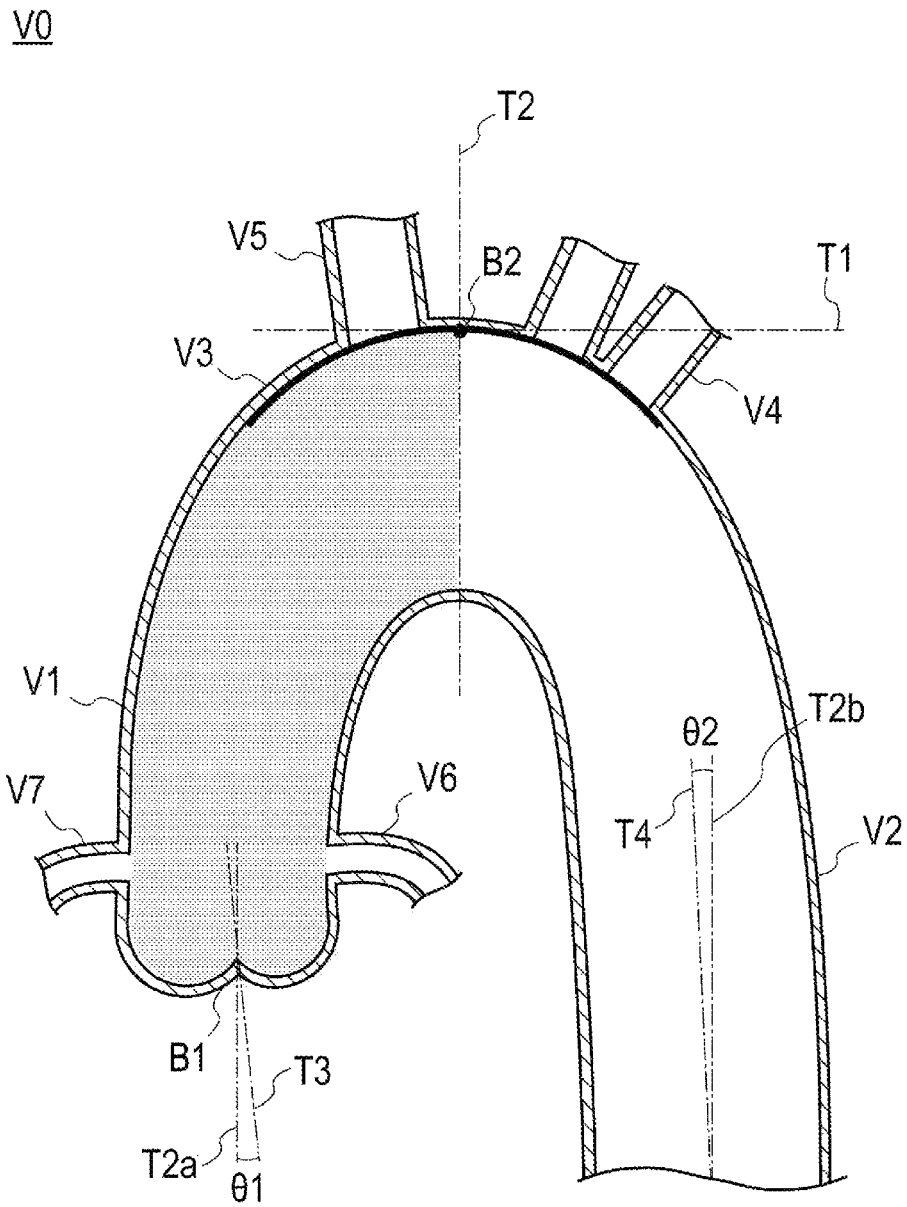

[FIG. 6B]
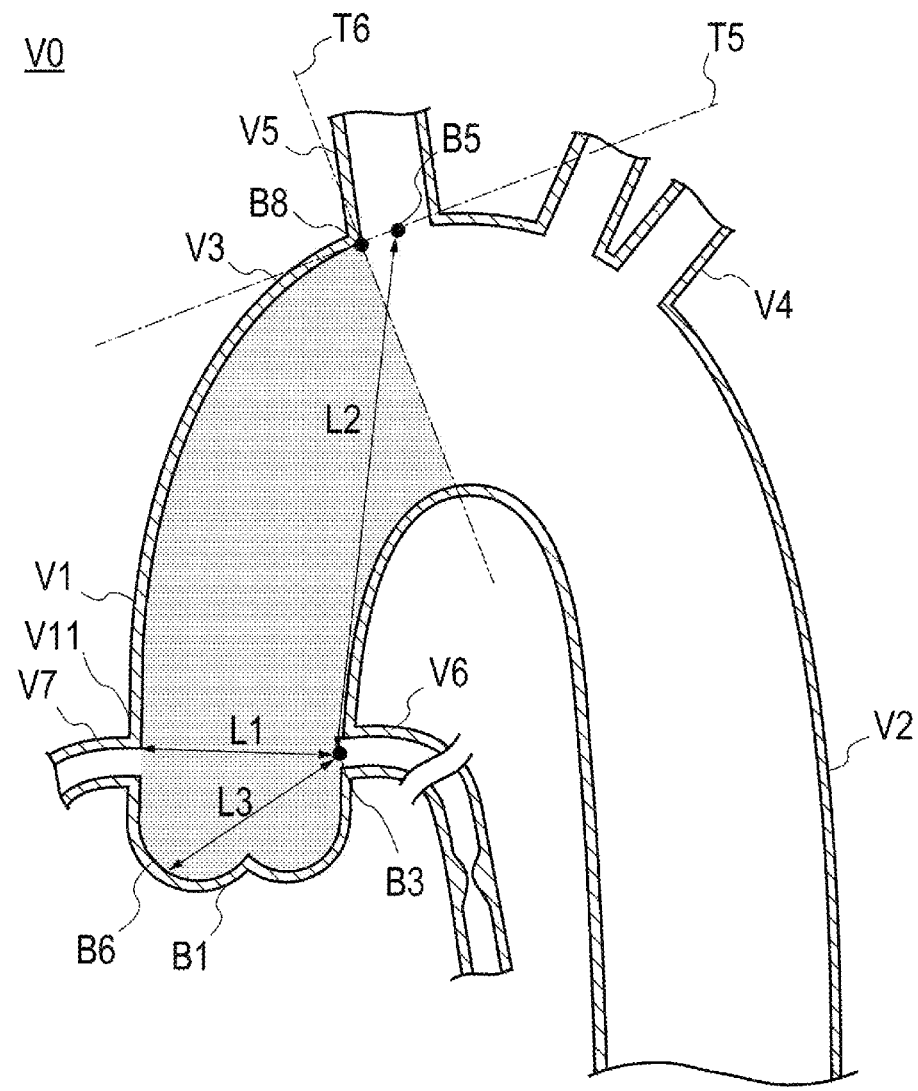
[FIG. 6C]
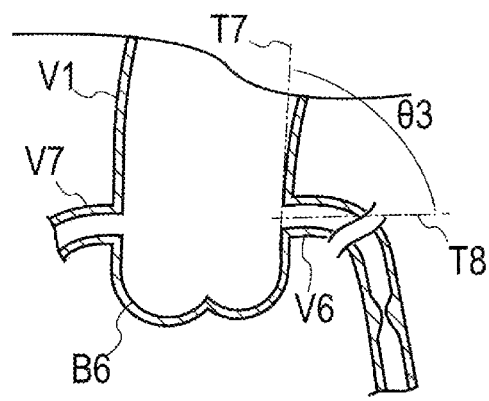

[FIG. 6D]
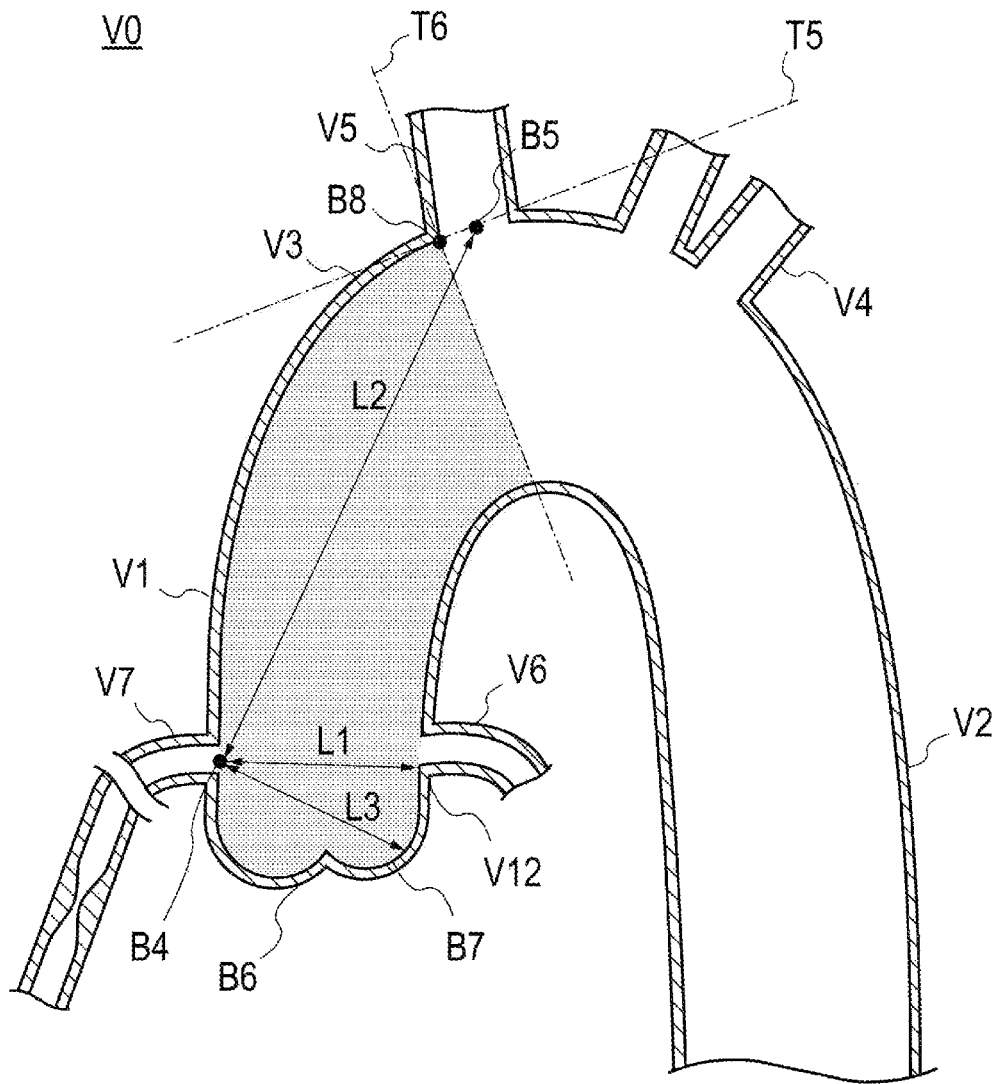
[FIG. 6E]
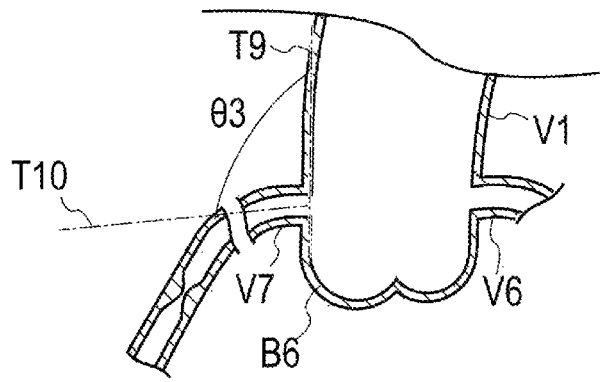

[FIG. 7]
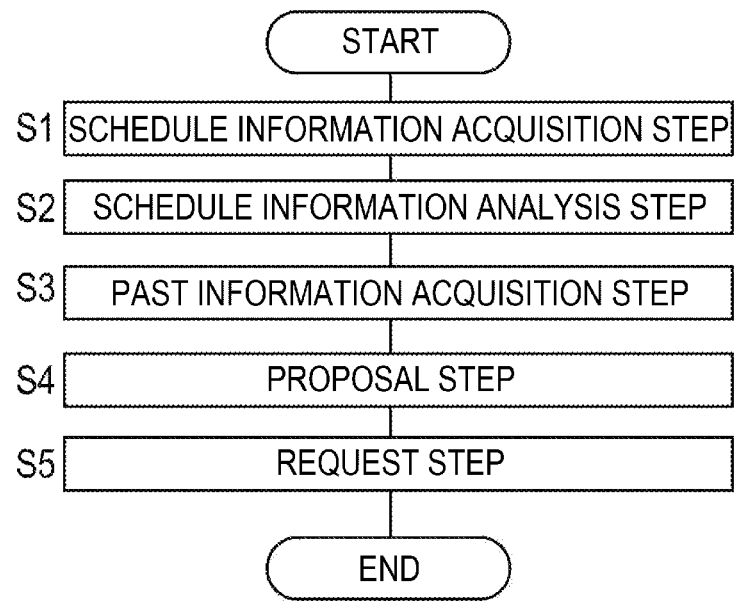

ASSISTANCE SYSTEM, ASSISTANCE METHOD, ASSISTANCE PROGRAM, AND RECORDING MEDIUM HAVING ASSISTANCE PROGRAM RECORDED THEREON

TECHNICAL FIELD

The present invention relates to an assistance system, an assistance method, an assistance program, and a recording medium having an assistance program recorded thereon, which assist a doctor by proposing a catheter used for a surgery to the doctor.

BACKGROUND ART

In recent years, surgeries are known such as percutaneous coronary intervention (PCI) and percutaneous transluminal coronary angioplasty (PTCA) which treat a lesion area inside a coronary artery by using a catheter. In the PCI and PTCA surgeries, a distal portion of a guiding catheter engages with an entrance of a coronary artery, and a contrast agent and various devices are introduced into the coronary artery through a lumen of the guiding catheter. In this manner, the lesion area inside the coronary artery is diagnosed and treated (for example, refer to PTL 1 below).

CITATION LIST

Patent Literature

PTL 1: JP-A-5-154202

SUMMARY OF INVENTION

Technical Problem

In the surgery using this guiding catheter, in order to smoothly introduce various treatment devices into the coronary artery, the guiding catheter needs a backup force for blocking a reaction generated when various devices are introduced or when various devices pass through a stenosed site.

The guiding catheter comes into contact with a blood vessel wall of a patient, thereby generating the backup force in the guiding catheter. Therefore, a magnitude of the backup force is affected by a vascular shape of the patient and a shape of the guiding catheter. Therefore, it is difficult for a doctor (particularly, a doctor having little experience in the surgery) to select a suitable guiding catheter before the surgery. Therefore, during the surgery, in a case where a surgeon determines that the guiding catheter in use does not ensure a suitable backup force, the surgeon takes measures to replace the guiding catheter in use with a guiding catheter having another shape, thereby hindering a rapid surgery.

The present invention is made in view of the above-described circumstances, and aims to provide an assistance system, an assistance method, an assistance program, and a recording medium having an assistance program recorded thereon, which can propose a catheter suitable for a surgery before the surgery.

Solution to Problem

According to the present invention, in order to achieve the above-described object, there is provided an assistance system for assisting a doctor by proposing a shape of a catheter to be used for a surgery of a patient. The assistance system includes a schedule information acquisition unit that acquires disease information on the surgery and a blood vessel information relating to a shape of a portion capable of applying a backup force to the catheter by coming into contact with the catheter in a blood vessel of the patient, a past information acquisition unit that acquires a shape of the catheter used for a past similar surgery having the disease information coinciding with that of the surgery and having the blood vessel information similar to that of the surgery, and a proposal unit that corrects the shape of the catheter used for the past similar surgery, based on a comparison result obtained by comparing the blood vessel information on the surgery with the blood vessel information on the past similar surgery, and that proposes the catheter having the corrected shape, as the catheter to be used for the surgery.

According to the present invention, in order to achieve the above-described object, there is provided an assistance method for assisting a doctor by proposing a shape of a catheter to be used for a surgery of a patient. The assistance method includes a schedule information acquisition step of acquiring disease information on the surgery and a blood vessel information relating to a shape of a portion capable of applying a backup force to the catheter by coming into contact with the catheter in a blood vessel of the patient, a past information acquisition step of acquiring a shape of the catheter used for a past similar surgery having the disease information coinciding with that of the surgery and having the blood vessel information similar to that of the surgery, and a proposal step of correcting the shape of the catheter used for the past similar surgery, based on a comparison result obtained by comparing the blood vessel information on the surgery with the blood vessel information on the past similar surgery, and proposing the catheter having the corrected shape, as the catheter to be used for the surgery.

According to the present invention, in order to achieve the above-described object, there is provided an assistance program for assisting a doctor by proposing a shape of a catheter to be used for a surgery of a patient. The assistance program includes a procedure of acquiring disease information on the surgery and a blood vessel information relating to a shape of a portion capable of applying a backup force to the catheter by coming into contact with the catheter in a blood vessel of the patient, a procedure of acquiring a shape of the catheter used for a past similar surgery having the disease information coinciding with that of the surgery and having the blood vessel information similar to that of the surgery, and a procedure of correcting the shape of the catheter used for the past similar surgery, based on a comparison result obtained by comparing the blood vessel information on the surgery with the blood vessel information on the past similar surgery, and proposing the catheter having the corrected shape, as the catheter to be used for the surgery.

According to the present invention, in order to achieve the above-described object, there is provided a computer-readable recording medium having the assistance program recorded thereon.

Advantageous Effects of Invention

The present invention corrects a shape of a catheter used for a past similar surgery, based on a comparison result obtained by comparing blood vessel information on a scheduled surgery with blood vessel information on the past similar surgery, and proposes a catheter having the corrected shape, as a catheter to be used for the surgery. Therefore, the catheter suitable for the surgery can be proposed before the surgery.

BRIEF DESCRIPTION OF DRAWINGS

FIG. 1 is a view illustrating an outline of an assistance system according to the present embodiment.

FIG. 2A is a block diagram illustrating a hardware configuration of the assistance system according to the present embodiment.

FIG. 2B is a block diagram illustrating a functional configuration of the assistance system according to the present embodiment.

FIG. 3 is a view illustrating past surgery information of the assistance system according to the present embodiment.

FIG. 4A is a view for describing a backup force of a guiding catheter.

FIG. 4B is a view for describing the backup force of the guiding catheter.

FIG. 5A is a view for describing a dimension of a Judkins Left type catheter.

FIG. 5B is a view for describing a dimension of an Amplatz Left type catheter.

FIG. 5C is a view for describing a dimension of an Ikari Left type catheter.

FIG. 6A is a view for describing blood vessel information of the assistance system according to the present embodiment.

FIG. 6B is a view for describing the blood vessel information of the assistance system according to the present embodiment.

FIG. 6C is a view for describing the blood vessel information of the assistance system according to the present embodiment.

FIG. 6D is a view for describing the blood vessel information of the assistance system according to the present embodiment.

FIG. 6E is a view for describing the blood vessel information of the assistance system according to the present embodiment.

FIG. 7 is a flowchart illustrating an assistance method according to the present embodiment.

DESCRIPTION OF EMBODIMENTS

Hereinafter, an embodiment according to the present invention will be described with reference to the accompanying drawings. In the description of the drawings, the same reference numerals will be assigned to the same elements, and repeated description will be omitted. In addition, dimensional ratios in the drawing are exaggerated for convenience of the description, and may be different from actual ratios in some cases.

FIG. 1 is a view for describing an outline of an assistance system 100 according to the present embodiment. FIGS. 2A and 2B are views for describing each unit of the assistance system 100. FIGS. 3, 4A, 4B, 5A to 5C, and 6A to 6E are views for describing information handled by the assistance system 100.

As illustrated in FIG. 1, the assistance system 100 proposes a guiding catheter C1 for a coronary artery which is suitable for a scheduled surgery by using past surgery information D1. As illustrated in FIGS. 4A and 4B, a guiding catheter for the coronary artery (indicated by C0 in the drawing) is a catheter indwelling in a state where a distal portion thereof engages with an entrance of coronary arteries V6 and V7 bypassing through an aorta V0. A surgeon introduces a contrast agent and various treatment devices into the coronary arteries V6 and V7 through a lumen of the indwelling guiding catheter for the coronary artery, and diagnoses and treats a lesion area N inside the coronary arteries V6 and V7. Hereinafter, in the present embodiment, the guiding catheter for the coronary artery will be simply referred to as a "catheter".

As illustrated in FIG. 1, the assistance system 100 is connected to a plurality of intra-hospital terminals 200 via an intra-hospital network NW1, and is configured to function as a server that transmits and receives data between the intra-hospital terminals 200. In addition, the assistance system 100 is connected to a supplier 300 of the catheter via an out-of-hospital network NW2, and can request the supplier 300 to manufacture the proposed catheter C1. A user of the assistance system 100 can operate one of the intra-hospital terminals 200 (operation terminals), can propose the catheter C1 to be used for a surgery to the assistance system 100, and can request the supplier 300 to manufacture the proposed catheter C1. Hereinafter, the assistance system 100 will be described in detail.

First, a hardware configuration of the assistance system 100 will be described.

As illustrated in FIG. 2A, the assistance system 100 includes a central processing unit (CPU) 110, a storage unit 120, an input-output I/F 130, a communication unit 140, and a reading unit 150. The CPU 110, the storage unit 120, the input-output I/F 130, the communication unit 140, and the reading unit 150 are connected to a bus 160, and exchange data with each other via the bus 160. Hereinafter, each unit will be described.

The CPU 110 controls each unit, and performs various arithmetic processes in accordance with various programs stored in the storage unit 120.

The storage unit 120 is configured to include a read only memory (ROM) for storing various programs or various data items, a random access memory (RAM) for temporarily storing programs or data as a work region, and a hard disk for storing various programs including an operating system or various data items.

Although not particularly limited, the input-output I/F 130 is an interface for connecting an input device such as a keyboard and a mouse and an output device such as a display and a printer to each other, for example.

The communication unit 140 is an interface for communicating with the plurality of intra-hospital terminals 200 and the supplier 300.

The reading unit 150 reads data recorded on a computer-readable recording medium MD (refer to FIG. 1). Although not particularly limited, the computer-readable recording medium MD can be configured to include an optical disk such as a CD-ROM and a DVD-ROM, a USB memory, or an SD memory card, for example. Although not particularly limited, the reading unit 150 can be configured to include a CD-ROM drive or a DVD-ROM drive, for example.

Next, a main function of the assistance system 100 will be described.

The storage unit 120 stores an assistance program that proposes the catheter to be used for the surgery. According to the present embodiment, the assistance program is provided by a computer-readable recording medium MD.

The storage unit 120 stores past surgery information D1 relating to surgeries performed by an intra-hospital doctor in the past.

As illustrated in FIG. 3, the past surgery information D1 includes information on a surgery number (described as "No" in the drawing), disease information, lesion area information, blood vessel information, a shape of the used catheter C0, an access site, and other device information (not illustrated).

The information is stored in the storage unit 120 in a state of being associated with each surgery.

For example, the disease information can include a disease name and a disease site.

The lesion area information is not particularly limited as long as it is possible to extract a state of the lesion area (for example, in a case where a blood vessel is stenosed, a position of a stenosed site inside the blood vessel, a length of the stenosed site, a stenosed degree of the stenosed site, and the presence or absence of calcification at the stenosed site). For example, the lesion area information can be configured to include a lesion area image captured using methods of angiography such as coronary angiography (CAG), X-ray, CT, or MRI.

The blood vessel information is not particularly limited as long as it is possible to extract a shape of a portion capable of applying a backup force to the catheter C0 by coming into contact with the catheter C0 in the blood vessel of the patient. For example, the blood vessel information can be configured to include a blood vessel image captured using methods of the angiography such as the CAG, the X-ray, the CT, or the MRI. For example, as illustrated in FIG. 4A, in a case where a lesion area N is located inside the left coronary artery V6, a surgeon causes a distal portion of the catheter C0 to engage with an entrance of the left coronary artery V6. In this case, an inner wall V11 of an ascending aorta V1 facing the entrance of the coronary artery V6 corresponds to the portion capable of applying the backup force to the catheter C0 by coming into contact with the catheter C0 in the blood vessel of the patient. In addition, for example, as illustrated in FIG. 4B, in a case where the lesion area N is located inside the right coronary artery V7, the surgeon causes the distal portion of the catheter C0 to engage with an entrance of the right coronary artery V7. In this case, an inner wall V12 of the ascending aorta V1 facing the entrance of the coronary artery V7 corresponds to the portion capable of applying the backup force to the catheter C0 by coming into contact with the catheter C0 in the blood vessel of the patient. In this way, in a case where the lesion area N is located inside the coronary arteries V6 and V7, the blood vessel information can be configured to include aorta information (aorta image) relating to a shape of the aorta V0 including the inner walls V11 and V12 of the ascending aorta V1 facing the entrance of the coronary arteries V6 and V7.

The lesion area information may be included in the blood vessel information. That is, the aorta image may include not only the aorta but also the lesion area and the coronary artery.

The shape of the used catheter C0 is not particularly limited as long as the shape includes information relating to the shape of the portion generating the backup force to the catheter C0 by coming into contact with a blood vessel wall in the catheter C0. According to the present embodiment, the distal portion of the catheter C0 generates the backup force in the catheter C0. Accordingly, for example, as illustrated in FIG. 3, the shape of the catheter C0 includes a basic shape of the distal portion of the catheter C0, a dimension of the distal portion of the catheter C0, and an outer diameter of the catheter C0. For example, the basic shape of the distal portion of the catheter C0 includes Judkins Left (JL), Amplatz Left (AL), Ikari Left (IL), Judkins Right (JR), and Amplatz Right (AR). In the description herein, the distal portion refers to an end portion (distal end) of the catheter on a side inserted into the blood vessel of the patient and a prescribed range from the distal end. For example, in a case where the basic shape is JL, as illustrated in FIG. 5A, the dimension of the distal portion of the catheter C0 is set as follows. When a position of a first bending portion is set to a first point P1, a position of a second bending portion is set to a second point P2, and a position of a third bending portion is set to a third point P3 sequentially from the distal side, the dimension of the distal portion of the catheter C0 includes a distance X1 between the first point P1 and the second point P2 and a distance X2 between the second point P2 and the third point P3. In addition, for example, in a case where the basic shape is AL, as illustrated in FIG. 5B, the dimension of the distal portion of the catheter C0 is set as follows. When the position of the first bending portion is set to the first point P1 and the position of the second bending portion is set to the second point P2 sequentially from the distal side, the dimension of the distal portion of the catheter C0 includes the distance X1 between the first point P1 and the second point P2, and a curvature radius R1 of the second bending portion. In addition, for example, in a case where the basic shape is IL, as illustrated in FIG. 5C, the dimension of the distal portion of the catheter C0 is set as follows. When the position of the first bending portion is set to the first point P1, the position of the second bending portion is set to the second point P2, the position of the third bending portion is set to the third point P3, and a position of a fourth bending portion is set to a fourth point P4 sequentially from the distal side, the dimension of the distal portion of the catheter C0 includes the distance X1 between the first point P1 and the second point P2, the distance X2 between the second point P2 and the third point P3, and a distance X3 between the third point P3 and the fourth point P4. The dimension of the distal portion of the catheter C0 and the outer diameter of the catheter C0 may be stored in the storage unit 120 as numerical data, or an image of the catheter C0 may be stored in the storage unit 120 so that the above-described dimension is extracted from the image of the catheter C0.

The access site is not particularly limited as long as the access site indicates a puncture position for inserting the catheter C0 into a blood vessel. For example, as illustrated in FIG. 3, the access site includes a right arm radial artery (right radial), a left arm radial artery (left radial), a right femoral artery (right Femoral), and a left femoral artery (left Femoral).

Other device information can include the outer diameter and the length of the device inserted into the lumen of the catheter C0 during the surgery.

The storage unit 120 stores introducer information relating to a plurality of types of introducers. The introducer information can include an inner diameter of a sheath included in the introducer.

As illustrated in FIG. 2B, the CPU 110 executes an assistance program stored in the storage unit 120. In this manner, the CPU 110 functions as a schedule information acquisition unit 111, a schedule information analysis unit 112, a past information acquisition unit 113, a proposal unit 114, and a request unit 115. Hereinafter, each unit will be described.

First, the schedule information acquisition unit 111 will be described.

As illustrated in FIG. 1, the schedule information acquisition unit 111 acquires surgery schedule information D2 relating to a scheduled surgery from the intra-hospital terminal 200 operated by a user.

For example, the surgery schedule information D2 can include disease information on the scheduled surgery, lesion area information, blood vessel information (aorta information), and a scheduled access site. The disease information can include a disease name and a disease site, as in the past surgery information. As in the past surgery information, the lesion area information is not particularly limited as long as it is possible to recognize a state of a lesion area. For example, the lesion area information can be configured to include a lesion area image captured using methods of the angiography such as the CAG, the X-ray, the CT, or the MRI. As in the past surgery information, the blood vessel information is not particularly limited as long as the blood vessel information can extract the shape of the portion capable of applying the backup force to the catheter by coming into contact with the catheter in the blood vessel of the patient. For example, the blood vessel information can be configured to include a blood vessel image (aorta image) captured using methods of the angiography such as the CAG, the X-ray, the CT, or the MRI.

Next, the schedule information analysis unit 112 will be described.

As illustrated in FIG. 6A, based on the blood vessel information, the schedule information analysis unit 112 calculates a volume of the ascending aorta V1, an angle θ1 of the ascending aorta V1, an angle θ2 of the descending aorta V2, and a curvature of an outer portion of an aortic arch V3. For example, the schedule information analysis unit 112 calculates a volume of a portion (portion shaded in gray in the drawing) surrounded by an aortic valve B1 and a plane T2 orthogonal to a tangent plane T1 passing through a vertex B2 of the aortic arch V3 in the aorta V0 of the aorta V0, as a volume of the ascending aorta V1. In addition, for example, the schedule information analysis unit 112 calculates the angle θ1 of an axis T3 of the aortic valve B1 with respect to a straight line T2a parallel to the plane T2, as the angle θ1 of the ascending aorta V1. In addition, for example, the schedule information analysis unit 112 approximates a central axis of the descending aorta V2 with a straight line T4, and calculates the angle θ2 of the approximated straight line T4 with respect to a straight line T2b parallel to the plane T2, as the angle θ2 of the descending aorta V2. In addition, for example, the schedule information analysis unit 112 circularly approximates a portion including at least the vertex B2 and an entrance of a left subclavian artery V4 on the inner wall outside the aortic arch V3 (upper side of the body), and can calculate a reciprocal number of the radius of the approximated circle, as the curvature of the outer portion of the aortic arch V3. In the present embodiment, the schedule information analysis unit 112 circularly approximates a portion (portion indicated by a thick curve in the drawing) including an entrance of a brachiocephalic artery V5, the vertex B2, and an entrance of a left subclavian artery V4 on the inner wall outside the aortic arch V3, and calculates the reciprocal number of the radius of the approximated circle, as the curvature of the outer portion of the aortic arch V3. The above-described calculation method is an example. The calculation method of the volume of the ascending aorta V1, the angle θ1 of the ascending aorta V1, the angle θ2 of the descending aorta V2, and the curvature of the outer portion of the aortic arch V3 is not particularly limited as long as the calculation method can evaluate the volume of the ascending aorta V1, the angle θ1 of the ascending aorta V1, the angle θ2 of the descending aorta V2, and the curvature of the outer portion of the aortic arch V3.

In addition, as illustrated in FIGS. 6B and 6D, based on the blood vessel information, the schedule information analysis unit 112 calculates a distance L1 from the entrance of the coronary arteries V6 and V7 with which the distal portion of the catheter C1 engages to inner walls V11 and V12 of the ascending aorta V1 facing the entrance of the coronary arteries V6 and V7 (hereinafter, simply referred to as the "distance L1 to the inner wall of the ascending aorta V1"), a distance L2 from the entrance of the coronary arteries V6 and V7 with which the distal portion of the catheter C1 engages to the entrance of the brachiocephalic artery V5 (hereinafter, simply referred to as the "distance L2 to the brachiocephalic artery V5"), and a distance L3 from the entrance of the coronary arteries V6 and V7 with which the distal portion of the catheter C1 engages to inner wall of the valsalva sinus B6 and B7 facing the entrance of the coronary arteries V6 and V7 (hereinafter, simply referred to as the "distance L3 to the valsalva sinus").

With regard to above-described dimensions, referring to FIG. 6B, a case where the distal portion of the catheter C1 engages with the entrance of the left coronary artery V6 will be described as an example. For example, the distance L1 to the ascending aorta V1 can be defined as the distance L1 from a center point B3 of the entrance of the left coronary artery V6 to the inner wall V11 of the ascending aorta V1 facing the left coronary artery V6. For example, the distance L2 to the brachiocephalic artery V5 can be defined as the distance L2 from the center point B3 of the entrance of the left coronary artery V6 to a center point B5 of the entrance of the brachiocephalic artery V5. For example, the distance L3 to the valsalva sinus can be defined as the distance L3 from the center point B3 of the entrance of the left coronary artery V6 to the valsalva sinus B6 facing the left coronary artery V6.

In addition, with regard to the above-described dimensions, referring to FIG. 6D, a case where the distal portion of the catheter C1 engages with the entrance of the right coronary artery V7 will be described as an example. For example, the distance L1 to the ascending aorta V1 can be defined as the distance L1 from the center point B4 of the entrance of the right coronary artery V7 to the inner wall V12 of the ascending aorta V1 facing the right coronary artery V7. For example, the distance L2 to the brachiocephalic artery V5 can be defined as the distance L2 from the center point B4 of the entrance of the right coronary artery V7 to the center point B5 of the entrance of the brachiocephalic artery V5. For example, the distance L3 to the valsalva sinus can be defined as the distance L3 from the center point B4 of the entrance of the right coronary artery V7 to the valsalva sinus B7 facing the right coronary artery V7.

In addition, based on the blood vessel information, the schedule information analysis unit 112 calculates an angle θ3 formed between the ascending aorta V1 and the coronary arteries V6 and V7 with which the distal portion of the catheter engages (hereinafter, simply referred to as the "angle θ3 of the coronary artery") and the inner diameter of the entrance of the coronary arteries V6 and V7. For example, as illustrated in FIG. 6C, in a case where the distal portion of the catheter C1 engages with the entrance of the left coronary artery V6, the schedule information analysis unit 112 calculates the angle θ3 of a central axis T8 of a root of the left coronary artery V6 with respect to a tangent plane T7 of the entrance of the left coronary artery V6, as the angle θ3 of the coronary artery. In addition, for example, as illustrated in FIG. 6E, in a case where the distal portion of the catheter C1 engages with the entrance of the right coronary artery V7, the schedule information analysis unit 112 calculates the angle θ3 of a central axis T10 of a root of the right coronary artery V7 with respect to a tangent plane T9 of the entrance of the right coronary artery V7, as the angle θ3 of the coronary artery.

Next, the past information acquisition unit 113 will be described.

Based on the past surgery information D1 stored in the storage unit 120, the past information acquisition unit 113 acquires the past similar surgery having the disease information coinciding with that of the scheduled surgery, and having the access site coinciding with that of the scheduled surgery, and having the blood vessel information similar to that of the scheduled surgery. In the description herein, the similarity of the blood vessel information means that a coincidence rate between a vascular shape in the scheduled surgery and a vascular shape in the past surgery falls within a predetermined range. Specifically, for example, according to the present embodiment, the similarity is determined when the coincidence rate of the volume of the ascending aorta V1 between the vascular shape in the scheduled surgery and the vascular shape in the past surgery, and the coincidence rate of the angle θ1 of the ascending aorta V1, the coincidence rate of the angle θ2 of the descending aorta V2, and the coincidence rate of the curvature of the outer portion of the aortic arch V3 are equal to or greater than a predetermined lower limit value. As in the schedule information analysis unit 112, based on the blood vessel information, the past information acquisition unit 113 calculates the volume of the ascending aorta V1, the angle θ1 of the ascending aorta V1, the angle θ2 of the descending aorta V2, and the curvature of the outer portion of the aortic arch V3.

As illustrated in FIGS. 6B to 6E, based on the blood vessel information on the past similar surgery, the past information acquisition unit 113 calculates the distance L1 to the inner wall of the ascending aorta V1, the distance L2 to the brachiocephalic artery V5, the distance L3 to the valsalva sinus, the angle θ3 of the coronary artery, and the inner diameter of the entrance of the coronary arteries V6 and V7.

Next, the proposal unit 114 will be described.

As illustrated in FIG. 2B, the proposal unit 114 is provided with a function as the basic shape determination unit 114a that determines the basic shape of the catheter C1 to be used for the scheduled surgery and the shape optimization unit 114b that corrects the determined basic shape and proposes the catheter C1 having the corrected shape, as the catheter C1 to be used for the scheduled surgery.

The basic shape determination unit 114a calculates the coincidence rate of the distance L1 to the inner wall of the ascending aorta V1, the coincidence rate of the distance L2 to the brachiocephalic artery V5, the coincidence rate of the distance L3 to the valsalva sinus, the coincidence rate of the angle θ3 of the coronary artery, and the coincidence rate of the inner diameter of the entrance of the coronary arteries V6 and V7 between the scheduled surgery and the past similar surgery.

The basic shape determination unit 114a multiplies the respectively calculated coincidence rates by a weighting coefficient, adds values multiplied by the weighting coefficient, and calculates the added value as a score determined in accordance with the coincidence rates of the vascular shapes between the scheduled surgery and the past similar surgery. A value of the weighting coefficient is not particularly limited. For example, in a case where a state of the lesion area is complete chronic occlusion, the weighting coefficient of the coincidence rate of the distance L1 to the inner wall of the ascending aorta V1 can be set to a value greater than 1.

The basic shape determination unit 114a extracts the surgery having the highest score in the past similar surgery. In this manner, the past similar surgery having the vascular shape most similar to that of the scheduled surgery can be extracted. The basic shape determination unit 114a acquires the shape of the catheter C0 (the basic shape of the distal portion, and the dimension and the outer diameter of the distal portion) in the surgery having the highest score, and sets the shape as the basic shape of the catheter C1 to be used for the scheduled surgery.

The shape optimization unit 114b corrects the base shape determined by the basic shape determination unit 114a, based on a comparison result of the distance L1 to the inner wall of the ascending aorta V1, a comparison result of the distance L2 to the brachiocephalic artery V5, and a comparison result of the distance L3 to the valsalva sinus, between the scheduled surgery and the surgery having the highest score. The shape optimization unit 114b proposes the catheter C1 having the corrected basic shape to the user, as the catheter C1 used for the scheduled surgery.

A correction method of the basic shape by the shape optimization unit 114b will be described with reference to a case where the access site of the scheduled surgery is the radial artery or the femoral artery of the left arm and the basic shape is JL. In the following example, the distance L1 to the inner wall of the ascending aorta V1 in the scheduled surgery is shorter than the distance L1 to the inner wall of the ascending aorta V1 in the surgery having the highest score. The shape optimization unit 114b calculates a difference δL1 in the distances L1 to the inner wall of the ascending aorta V1 between the surgery having the highest score and the scheduled surgery. As illustrated in FIG. 5A, the shape optimization unit 114b subtracts the difference δL1 in the distances L1 from the distance X1 between the first point P1 and the second point P2 of the catheter C0 used for the surgery having the highest score. The shape optimization unit 114b corrects a position of the second point P2 so that a subtracted value is a distance X11 between the first point P1 and the second point P2 of the catheter C1 to be used for the scheduled surgery. In addition, the shape optimization unit 114b calculates a ratio of the distance X11 between the first point P1 and the second point P2 of the catheter in which the position of the second point is corrected with respect to the distance X1 between the first point P1 and the second point P2 of the catheter C0 used for the surgery having the highest score. The shape optimization unit 114b multiplies the calculated ratio by the distance X2 between the second point P2 and the third point P3 of the catheter C0 used for the surgery having the highest score. The shape optimization unit 114b corrects the position of the third point P3 so that the multiplied value is the distance X21 between the second point P2 and the distance X21 of the third point P3 of the catheter C1 to be used for the surgery. In a case where the distance L1 to the inner wall of the ascending aorta V1 in the scheduled surgery is longer than the distance L1 to the inner wall of the ascending aorta V1 in the surgery having the highest score, the shape optimization unit 114b adds the difference δL1 of the distance L1 to the distance X1 between the first point P1 and the second point P2 of the catheter C0 used in the surgery having the highest score.

Next, a correction method of the basic shape by the shape optimization unit 114b will be described with reference to a case where the access site in the scheduled surgery is the radial artery of the right arm and the basic shape determined by the basic shape determination unit 114a is AL. In the following example, the distance L1 to the inner wall of the ascending aorta V1 in the scheduled surgery is shorter than the distance L1 to the inner wall of the ascending aorta V1 in the surgery having the highest score. The distance L3 to the valsalva sinus in the scheduled surgery is shorter than the distance L3 to the valsalva sinus in the surgery having the highest score. The shape optimization unit 114b calculates a difference δL2 from a half of the distance L1 to the inner wall of the ascending aorta V1 between the surgery having the highest score and the scheduled surgery. The shape optimization unit 114b subtracts the difference δL2 in the distance L1 from a curvature radius R1 of the second bending portion of the catheter C0 used for the surgery having the highest score. The shape optimization unit 114b corrects the curvature radius of the second bending portion so that the subtracted value is a curvature radius R11 of the second bending portion of the catheter C1 to be used for the scheduled surgery. The shape optimization unit 114b calculates a difference δL3 in the distance L3 to the valsalva sinus between the surgery having the highest score and the scheduled surgery. The shape optimization unit 114b subtracts the difference δL3 in the distance L3 from the distance X1 between the first point P1 and the second point P2 of the catheter used for the surgery having the highest score. The shape optimization unit 114b corrects the position of the first point P1 so that the subtracted value is the distance X11 between the first point P1 and the second point P2 of the catheter C1 to be used for the scheduled surgery. In a case where the distance L1 to the inner wall of the ascending aorta V1 in the scheduled surgery is longer than the distance L1 to the inner wall of the ascending aorta V1 in the surgery having the highest score, the shape optimization unit 114b adds the difference δL2 in the distance L1 to the curvature radius R1 of the second bending portion of the catheter C0 used for the surgery having the highest score. In addition, in a case where the distance L3 to the valsalva sinus in the scheduled surgery is longer than the distance L3 to the valsalva sinus in the surgery having the highest score, the shape optimization unit 114b adds the difference δL3 in the distance L3 to the distance X1 between the first point P1 and the second point P2 of the catheter used for the surgery having the highest score.

Next, a correction method of the basic shape by the shape optimization unit 114b will be described with reference to a case where the access site in the scheduled surgery is the radial artery of the right arm and the basic shape determined by the basic shape determination unit 114a is IL. In the following example, the distance L1 to the inner wall of the ascending aorta V1 in the scheduled surgery is shorter than the distance L1 to the inner wall of the ascending aorta V1 in the surgery having the highest score. The shape optimization unit 114b calculates the difference δL1 in the distance L1 to the inner wall of the ascending aorta V1 between the surgery having the highest score and the scheduled surgery. The shape optimization unit 114b subtracts the difference δL1 in the distance L1 from the distance X1 between the first point P1 and the second point P2 of the catheter C0 used for the surgery having the highest score. The shape optimization unit 114b corrects the position of the second point P2 so that the subtracted value is the distance X11 between the first point P1 and the second point P2 of the catheter C1 to be used for the scheduled surgery. In addition, the shape optimization unit 114b calculates a ratio of the distance X11 between the first point P1 and the second point P2 of the catheter in which the position of the second point P2 is corrected with respect to the distance X1 between the first point P1 and the second point P2 of the catheter C0 used for the surgery having the highest score. The shape optimization unit 114b multiplies the calculated ratio by the distance X2 between the second point P2 and the third point P3 of the catheter C0 used for the surgery having the highest score. The shape optimization unit 114b corrects the position of the third point P3 so that the multiplied value is the distance X21 between the second point P2 and the third point P3 of the catheter C1 to be used for the surgery. In addition, the shape optimization unit 114b calculates a ratio of the distance L2 to the brachiocephalic artery V5 between the surgery having the highest score and the scheduled surgery. The shape optimization unit 114b multiplies the calculated ratio by the distance X3 between the third point P3 and the fourth point P4 of the catheter C0 used for the surgery having the highest score. The shape optimization unit 114b corrects the position of the fourth point P4 so that the multiplied value is the distance X31 between the third point P3 and the fourth point P4 of the catheter C1 to be used for the surgery. In a case where the distance L1 to the inner wall of the ascending aorta V1 in the scheduled surgery is longer than the distance L1 to the inner wall of the ascending aorta V1 in the surgery having the highest score, the shape optimization unit 114b adds the difference δL1 in the distance L1 to the distance X1 between the first point P1 and the second point P2 of the catheter C0 used for the surgery having the highest score.

In this way, the shape optimization unit 114b corrects the shape of the catheter, based on a comparison result of the vascular shapes in the scheduled surgery and the past similar surgery (particularly, a shape of the portion relating to backup force generation in the catheter in the blood vessel). The above-described correction method is an example, and the shape optimization unit 114b can appropriately change the correction method in accordance with the basic shape. For example, the shape optimization unit 114b may correct the basic shape, based on a comparison result of the angle θ3 of the coronary artery, between the scheduled surgery and the surgery having the highest score, and a comparison result of the inner diameter of the entrance of the coronary arteries V6 and V7.

In addition, the shape optimization unit 114b may calculate a minimum inner diameter of the catheter into which devices expected to be used for the surgery can be inserted, and a minimum thickness that can maintain predetermined strength, based on the other device information of the surgery having the highest score, and may correct the inner diameter, the thickness, and outer diameter of the basic shape, based on a calculation result. At this time, in a case where the introducer to be used for the surgery is determined, the shape optimization unit 114b may determine the outer diameter of the catheter, based on the inner diameter of the sheath included in the introducer to be used for the surgery. A surgeon can perform the more minimally invasive surgery by using the catheter C1 whose inner diameter and thickness are corrected in the surgery.

In addition, the shape optimization unit 114b may propose the introducer that can be used in combination with the catheter C1 to be used for the surgery, based on the outer diameter of the catheter C1 to be used for the surgery and the introducer information stored in the storage unit 120. In this manner, a user can efficiently select the introducer.

In the proposal unit 114, the shape of the catheter C0 used not only for the surgery having the highest score but also for the surgery having the highest score in top cases may be set as the basic shape of the catheter C1 to be used for the surgery. The proposal unit 114 may propose the catheters C1 having each corrected basic shape to the user, as the catheters C1 to be used for the surgery. In this manner, the user can select a preferred catheter from the plurality of proposed catheters C1.

Next, the request unit 115 will be described.

The request unit 115 requests the supplier 300 to manufacture the proposed catheter C1 via the communication unit 140 and the out-of-hospital network NW2 in a case where the user requests the manufacturing of the proposed catheter C1. Therefore, during the surgery, the user can perform the surgery by using the catheter C1 (custom-made catheter C1) suitable for the vascular shape of the patient. Therefore, during the surgery, the catheter C1 can indwell a predetermined position in the blood vessel of the patient, and can apply a sufficient backup force when various treatment devices are introduced through the lumen. Therefore, during the surgery, the surgeon can smoothly introduce a contrast agent and various treatment devices into the coronary artery via the catheter C1 indwelling the predetermined position in the blood vessel. In addition, even if the backup force cannot be sufficiently obtained, the surgeon does not need to replace the catheter C1 with a catheter having another shape. Therefore, it is possible to minimize the number of the catheters to be used.

FIG. 7 is a view for describing an assistance method according to the present embodiment. Hereinafter, the assistance method according to the present embodiment will be described with reference to FIG. 7.

The assistance method includes a schedule information acquisition step S1, a schedule information analysis step S2, a past information acquisition step S3, a proposal step S4, and a request step S5. Hereinafter, each step will be described.

First, the schedule information acquisition step S1 will be described.

First, as illustrated in FIG. 1, the schedule information acquisition unit 111 instructs the user to input the surgery schedule information D2 via a display 210 of the intra-hospital terminal 200 operated by the user. Next, the user inputs the surgery schedule information D2. Next, the schedule information acquisition unit 111 acquires the surgery schedule information from the intra-hospital terminal 200 operated by the user.

Next, the schedule information analysis step S2 will be described.

As illustrated in FIG. 6A, based on the blood vessel information, the schedule information analysis unit 112 calculates the volume of the ascending aorta V1, the angle θ1 of the ascending aorta V1, the angle θ2 of the descending aorta V2, and the curvature of the outer portion of the aortic arch V3. In addition, as illustrated in FIGS. 6B to 6E, based on the blood vessel information, the schedule information analysis unit 112 calculates the distance L1 to the inner wall of the ascending aorta V1, the distance L2 to the brachiocephalic artery V5, the distance L3 to the valsalva sinus, the angle θ3 of the coronary artery, and the inner diameter of the entrance of the coronary arteries V6 and V7.

Next, the past information acquisition step S3 will be described.

First, based on the past surgery information D1 stored in the storage unit 120, the past information acquisition unit 113 acquires the past similar surgery having the disease information coinciding with that of the scheduled surgery, having the access site coinciding with that of the scheduled surgery, and having the blood vessel information similar to that of the scheduled surgery.

Next, based on the blood vessel information on the past similar surgery, the past information acquisition unit 113 calculates the distance L1 to the inner wall of the ascending aorta V1, the distance L2 to the brachiocephalic artery V5, the distance L3 to the valsalva sinus, the angle θ3 of the coronary artery, and the inner diameter of the entrance of the coronary arteries V6 and V7.

Next, the proposal step S4 will be described.

First, the basic shape determination unit 114a calculates the coincidence rate of the distance L1 to the inner wall of the ascending aorta V1, the coincidence rate of the distance L2 to the brachiocephalic artery V5, the coincidence rate of the distance L3 to the valsalva sinus, the coincidence rate of the angle θ3 of the coronary artery, and the coincidence rate of the entrance of the coronary arteries V6 and V7 between the scheduled surgery and the past similar surgery.

Next, the basic shape determination unit 114a multiplies each calculated coincidence rate by the weighting coefficient, adds the value multiplied by the weighting coefficient, and calculates the added value, as the score determined in accordance with the coincidence rate of the vascular shape between the scheduled surgery and the past similar surgery.

Next, the basic shape determination unit 114a extracts the surgery having the highest score from the past similar surgery, and sets the shape of the catheter C0 used for the surgery having the highest score as the basic shape of the catheter C1 to be used for the scheduled surgery.

Next, the shape optimization unit 114b corrects the basic shape of the catheter C1 which is determined by the basic shape determination unit 114a, based on the comparison result of the distance L1 to the inner wall of the ascending aorta V1, the comparison result of the distance L2 to the brachiocephalic artery V5, the comparison result of the distance L3 to the valsalva sinus, and the comparison result of the inner diameter L4 of the ascending aorta, between the scheduled surgery and the surgery having the highest score. In this case, the shape optimization unit 114b may correct the inner diameter, the thickness, and the outer diameter of the basic shape, based on other device information on the surgery having the highest score.

Next, the shape optimization unit 114b proposes the catheter C1 having the corrected shape to the user, as the catheter C1 to be used for the scheduled surgery. In addition, in this case, the shape optimization unit 114b may propose the introducer that can be used in combination with the proposed catheter C1.

Next, the request step S5 will be described.

First, the user requests the manufacturing of the proposed catheter C1. Next, the request unit 115 requests the supplier 300 to manufacture the proposed catheter C1 via the communication unit 140 and the out-of-hospital network NW2.

Next, the supplier 300 manufactures the proposed catheter C1 before the scheduled surgery date, and sends the catheter C1 to the user. Next, the user receives the manufactured catheter C1, and performs the surgery. After the surgery, the information relating to the surgery performed using the manufactured catheter C1 (the disease information, the lesion area information, the catheter shape, the access site, and other device information) is stored in the storage unit 120, and the past surgery information D1 is updated.

As described above, the assistance system 100 according to the present embodiment assists the doctor by proposing the shape of the catheter C1 to be used for the surgery. The assistance system 100 includes the schedule information acquisition unit 111 that acquires the disease information on the surgery and the blood vessel information relating to the shape of the portion capable of applying the backup force to the catheter C1 by coming into contact with the catheter C1 used for the surgery in the blood vessel of the patient, the past information acquisition unit 113 that acquires the shape of the catheter C0 used for the past similar surgery having the disease information coinciding with that of the surgery and having the blood vessel information similar to that of the surgery, and the proposal unit 114 that corrects the shape of the catheter C0 used for the past similar surgery, based on the comparison result obtained by comparing the blood vessel information on the surgery with the blood vessel information on the past similar surgery, and that proposes the catheter C1 having the corrected shape, as the catheter C1 to be used for the surgery.

According to the above-described assistance system 100, based on the comparison result obtained by comparing the blood vessel information on the scheduled surgery with the blood vessel information on the past similar surgery, the shape of the catheter C0 used for the past similar surgery is corrected. The catheter C1 having the corrected shape is proposed as the catheter C1 to be used for the scheduled surgery. In this manner, the catheter suitable for the surgery can be proposed before the surgery.

In addition, the proposal unit 114 further includes the request unit 115 that requests the supplier to manufacture the catheter C1 to be used for the surgery proposed by the proposal unit 114. Therefore, the surgeon can use the custom-made catheter C1 for the surgery.

The catheter C1 to be used for the surgery is the coronary artery catheter in which the distal portion engages with the entrance of the coronary artery by passing through the aorta. The blood vessel information includes the aorta information relating to the shape of the aorta. The proposal unit 114 corrects the shape of the catheter C0 used for the past similar surgery, based on the comparison result obtained by comparing the aorta information on the surgery with the aorta information on the past similar surgery. The catheter C1 having the corrected shape is proposed as the catheter C1 to be used for the surgery. Therefore, the surgeon can use the suitable catheter C1 in the surgery to diagnose and treat the lesion area of the coronary artery.

In addition, the aorta information includes the volume of the ascending aorta, the angle of the ascending aorta, the angle of the descending aorta, and the curvature of the outer portion of the aortic arch. Therefore, the assistance system 100 can propose the catheter C1 suitable for the scheduled surgery by using the information.

In addition, the aorta information includes the distance from the entrance of the coronary artery to the inner wall of the ascending aorta facing the entrance of the coronary artery, the distance from the entrance of the coronary artery to the entrance of the brachiocephalic artery, and the distance from the entrance of the coronary artery to the inner wall of the valsalva sinus facing the entrance of the coronary artery. Therefore, the assistance system 100 can propose the catheter C1 suitable for the scheduled surgery by using the information.

In addition, the assistance method according to the present embodiment assists the doctor by proposing the shape of the catheter C1 to be used for the surgery of the patient. The assistance method includes the schedule information acquisition step S1 of acquiring the disease information on the surgery and the blood vessel information relating to the shape of the portion capable of applying the backup force to the catheter C1 by coming into contact with the catheter C1 in the blood vessel of the patient, the past information acquisition step S3 of acquiring the shape of the catheter C0 used for the past similar surgery having the disease information coinciding with that of the surgery and having the blood vessel information similar to that of the surgery, and the proposal step S4 of correcting the shape of the catheter C0 used for the past similar surgery, based on the comparison result obtained by comparing the blood vessel information on the surgery with the blood vessel information on the past similar surgery, and proposing the catheter C1 having the corrected shape, as the catheter C1 to be used for the surgery.

In addition, the assistance program according to the present embodiment assists the doctor by proposing the shape of the catheter C1 to be used for the surgery of the patient. The assistance program includes the procedure of acquiring the disease information on the surgery and the blood vessel information relating to the shape of the portion capable of applying the backup force to the catheter C1 by coming into contact with the catheter C1 in the blood vessel of the patient, the procedure of acquiring the shape of the catheter C0 used for the past similar surgery having the disease information coinciding with that of the surgery and having the blood vessel information similar to that of the surgery, and the procedure of correcting the shape of the catheter C0 used for the past similar surgery, based on the comparison result obtained by comparing the blood vessel information on the surgery with the blood vessel information on the past similar surgery, and proposing the catheter C1 having the corrected shape, as the catheter C1 to be used for the surgery.

In addition, the recording medium MD according to the present embodiment is the computer-readable recording medium having the assistance program recorded thereon.

According to the assistance method, the assistance program, and the recording medium MD having the assistance program recorded thereon, based on the comparison result obtained by comparing the blood vessel information on the surgery with the blood vessel information on the past similar surgery, the shape of the catheter C0 used for the past similar surgery is corrected, and the catheter C1 having the corrected shape is proposed as the catheter to be used for the surgery. Therefore, the catheter suitable for the surgery can be proposed before the surgery.

Hitherto, the assistance system, the assistance method, the assistance program, and the recording medium having the assistance program recorded thereon according to the present invention have been described with reference to the embodiments. Without being limited only to the respectively described configurations, the present invention can be appropriately modified based on the description in the appended claims.

For example, the means and the method for performing various processes in the assistance system may be realized by a dedicated hardware circuit or a programmed computer. In addition, the assistance program may be provided online via a network such as the Internet.

In addition, the catheter to which the assistance system, the assistance method, and the assistance program according to the present invention are applied is not particularly limited as long as the contrast agent and various treatment devices are introduced through the lumen. For example, the present invention is applicable to a guiding sheath.

In addition, the guiding catheter to which the assistance system, the assistance method, and the assistance program according to the present invention are applied is not limited to the coronary artery guiding catheter. The present invention may be applied to a lower limb guiding catheter used for the surgery when diagnosing and treating the lesion area in the blood vessel of a lower limb. In this case, the blood vessel information is not particularly limited as long as it is possible to extract the shape of the portion capable of applying the backup force to the guiding catheter by coming into contact with the lower limb guiding catheter in the blood vessel of the patient. For example, in a case of a crossover approach from a contralateral femoral artery, an iliac artery corresponds to the portion capable of applying the backup force to the guiding catheter by coming into contact with the lower limb guiding catheter in the blood vessel of the patient.

In addition, in the above-described embodiment, the past information acquisition unit acquires the past surgery having the access site coinciding with that of the scheduled surgery, as the similar surgery. However, the access sites may not coincide with each other.

In addition, the assistance system may be connected to a terminal of another hospital or a server of a regional medical care center via an out-of-hospital network. In this case, the storage unit may store the past surgery information obtained by doctors at other hospitals, and the assistance system may propose the catheter by using the past surgery information obtained by the doctors at other hospitals.

This application is based on Japanese Patent Application No. 2018-016151 filed on Feb. 1, 2018, the disclosure of which is incorporated by reference in its entirety.

REFERENCE SIGNS LIST 100 assistance system
111 schedule information acquisition unit
112 schedule information analysis unit
113 past information acquisition unit
114 proposal unit
115 request unit
300 supplier
B6, B7 valsalva sinus
C0 catheter used for past surgery
C1 catheter to be used for scheduled surgery (coronary artery catheter)
L1 distance from entrance of coronary artery to inner wall of ascending aorta facing entrance
L2 distance from entrance of coronary artery to entrance of brachiocephalic artery
L3 distance from entrance of coronary artery to valsalva sinus facing entrance
MD recording medium
V1 ascending aorta
V11, V12 inner wall of ascending aorta facing entrance
V2 descending aorta
V3 aortic arch
V5 brachiocephalic artery
V6, V7 coronary artery
θ1 angle of ascending aorta
θ2 angle of descending aorta

The invention claimed is:

1. An assistance system for assisting a doctor by proposing a shape of a catheter to be used for a surgery of a patient, the system comprising:
   a schedule information acquisition unit that acquires disease information on the surgery and a blood vessel information relating to a shape of a portion capable of applying a backup force to the catheter by coming into contact with the catheter in a blood vessel of the patient;
   a past information acquisition unit that acquires a shape of a catheter used for a past similar surgery having disease information coinciding with that of the surgery and having blood vessel information similar to that of the surgery; and
   a proposal unit that corrects the shape of the catheter used for the past similar surgery, based on a comparison result obtained by comparing the blood vessel information on the surgery with the blood vessel information on the past similar surgery, and that proposes the catheter having the corrected shape, as the catheter to be used for the surgery.

2. The assistance system according to claim 1, further comprising:
   a request unit that requests a supplier to manufacture the catheter proposed by the proposal unit and to be used for the surgery.

3. The assistance system according to claim 1,
   wherein the catheter to be used for the surgery is a coronary artery catheter whose distal portion is configured to engage with an entrance of a coronary artery by passing through an aorta,
   wherein the blood vessel information similar to that of the surgery includes aorta information relating to a shape of the aorta, and
   wherein the proposal unit corrects the shape of the catheter used for the past similar surgery, based on a comparison result obtained by comparing aorta information on the surgery with the aorta information on the past similar surgery, and proposes the catheter having the corrected shape, as the catheter to be used for the surgery.

4. The assistance system according to claim 3,
   wherein the aorta information relating to the shape of the aorta from the blood vessel information on the past similar surgery includes a volume of an ascending aorta, an angle of the ascending aorta, an angle of a descending aorta, and a curvature of an outer portion of an aortic arch.

5. The assistance system according to claim 3,
   wherein the aorta information on the surgery and the aorta information on the past similar surgery includes a distance from the entrance of the coronary artery to an inner wall of an ascending aorta facing the entrance of the coronary artery, a distance from the entrance of the coronary artery to an entrance of a brachiocephalic artery, and a distance from the entrance of the coronary artery to an inner wall of a valsalva sinus facing the entrance of the coronary artery.

6. An assistance method for assisting a doctor by proposing a shape of a catheter to be used for a surgery of a patient, the method comprising:
   acquiring disease information on the surgery and a blood vessel information relating to a shape of a portion capable of applying a backup force to the catheter by coming into contact with the catheter in a blood vessel of the patient with a schedule information acquisition unit;
   acquiring a shape of a catheter used for a past similar surgery having disease information coinciding with that of the surgery and having blood vessel information similar to that of the surgery with a past information acquiring unit; and
   correcting the shape of the catheter used for the past similar surgery, based on a comparison result obtained by comparing the blood vessel information on the surgery with the blood vessel information on the past similar surgery, and proposing the catheter having the corrected shape, as the catheter to be used for the surgery with a proposal unit.

* * * * *